US006368642B2

(12) United States Patent
Kreiberg et al.

(10) Patent No.: US 6,368,642 B2
(45) Date of Patent: *Apr. 9, 2002

(54) COMPOSITION COMPRISING PECTIN METHYL ESTERASE AND TWO SUBSTRATES

(75) Inventors: Jette Dina Kreiberg, Roskilde; Tove Marte Ida Elsa Christensen, Allerod; Susanne Hyttel, Arhus C, all of (DK)

(73) Assignee: Danisco A/S, Copenhagen K (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/403,345

(22) PCT Filed: Apr. 24, 1998

(86) PCT No.: PCT/IB98/00673

§ 371 Date: Jan. 18, 2000

§ 102(e) Date: Jan. 18, 2000

(87) PCT Pub. No.: WO98/47391

PCT Pub. Date: Oct. 29, 1998

(30) Foreign Application Priority Data

Apr. 24, 1997 (GB) .............................. 9708278

(51) Int. Cl.$^7$ ............................................. A23L 1/0524
(52) U.S. Cl. ........................................ 426/50; 426/577
(58) Field of Search ......................... 426/61, 573, 577, 426/49, 50, 51, 52, 615, 616; 536/2

(56) References Cited

FOREIGN PATENT DOCUMENTS

| EP | 664303 A1 | 7/1995 |
|----|-----------|--------|
| WO | WO 93/09383 | 5/1993 |
| WO | WO 94/12055 | 6/1994 |
| WO | WO 94/25575 | 11/1994 |
| WO | WO 97/03574 | 2/1997 |
| WO | WO 97/31102 | 8/1997 |

OTHER PUBLICATIONS

Versteeg, et al J Food Sci 45 pp 969–971, Jan. 1980.
Pilnik and Voragen (Food Enzymology, Ed.:P.F.Fox; Elsevier; pp: 303–337), Jan. 1991.

*Primary Examiner*—Keith Hendricks
(74) *Attorney, Agent, or Firm*—Merchant & Gould P.C.

(57) ABSTRACT

A composition suitable for use as a foodstuff or in the preparation of a foodstuff is described. The composition includes a pectin methyl esterase (PME); a first PME substrate; and a second PME substrate; wherein neither the first PME substrate nor the second PME substrate originates in situ from the other.

19 Claims, 2 Drawing Sheets

SEQUENCE LISTING

<160> NUMBER OF SEQ ID NOS: 4

<210> SEQ ID NO 1
<211> LENGTH: 362
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 1

```
Met Ile Lys Asn Met Thr Asp Thr Asp Met Ile Met Arg Thr Ser
 1               5                  10                  15

Asn Asn Arg Lys Leu Ile Glu Glu Thr Ser Thr Val Asp Gly Trp Pro
            20                  25                  30

Ala Trp Leu Ser Thr Gly Asp Arg Arg Leu Leu Gln Ser Ser Ser Val
        35                  40                  45

Thr Pro Asn Val Val Ala Ala Asp Gly Ser Gly Asn Phe Lys Thr
    50                  55                  60

Val Ala Ala Val Ala Ala Pro Gln Gly Gly Thr Lys Arg Tyr
65                  70                  75                  80

Ile Ile Arg Ile Lys Ala Gly Val Tyr Arg Glu Asn Val Glu Val Thr
                85                  90                  95

Lys Lys His Lys Asn Ile Met Phe Ile Gly Asp Gly Arg Thr Arg Thr
                100                 105                 110

Ile Ile Thr Gly Ser Arg Asn Val Val Asp Gly Ser Thr Thr Phe Lys
            115                 120                 125

Ser Ala Thr Val Ala Val Val Gly Glu Gly Phe Leu Ala Arg Asp Ile
        130                 135                 140

Thr Phe Gln Asn Thr Ala Gly Pro Ser Lys His Gln Ala Val Ala Leu
145                 150                 155                 160

Arg Val Gly Ala Asp Leu Ser Ala Phe Tyr Asn Cys Asp Met Leu Ala
                165                 170                 175

Tyr Gln Asp Thr Leu Tyr Val His Ser Asn Arg Gln Phe Phe Val Asn
                180                 185                 190

Cys Leu Ile Ala Gly Thr Val Asp Phe Ile Phe Gly Asn Ala Ala Ala
            195                 200                 205

Val Leu Gln Asn Cys Asp Ile His Ala Arg Lys Pro Asn Ser Gly Gln
        210                 215                 220

Lys Asn Met Val Thr Ala Gln Gly Arg Ala Asp Pro Asn Gln Asn Thr
225                 230                 235                 240

Gly Ile Val Ile Gln Lys Ser Arg Ile Gly Ala Thr Ser Asp Leu Lys
                245                 250                 255

Pro Val Gln Gly Ser Phe Pro Thr Tyr Leu Gly Arg Pro Trp Lys Glu
                260                 265                 270

Tyr Ser Arg Thr Val Ile Met Gln Ser Ser Ile Thr Asp Val Ile His
            275                 280                 285

Pro Ala Gly Trp His Glu Trp Asp Gly Asn Phe Ala Leu Asn Thr Leu
        290                 295                 300

Phe Tyr Gly Glu His Gln Asn Ala Gly Ala Gly Ala Gly Thr Ser Gly
305                 310                 315                 320

Arg Val Lys Trp Lys Gly Phe Arg Val Ile Thr Ser Ala Thr Glu Ala
                325                 330                 335

Gln Ala Phe Thr Pro Gly Ser Phe Ile Ala Gly Ser Ser Trp Leu Gly
```

```
                    340              345              350
Ser Thr Gly Phe Pro Phe Ser Leu Gly Leu
            355              360
```

<210> SEQ ID NO 2
<211> LENGTH: 584
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

```
Met Thr Arg Ile Lys Glu Phe Phe Thr Lys Leu Ser Glu Ser Ser Thr
 1               5                  10                  15

Asn Gln Asn Ile Ser Asn Ile Pro Lys Lys Lys Lys Leu Phe Leu
             20                  25                  30

Ala Leu Phe Ala Thr Leu Leu Val Val Ala Ala Val Ile Gly Ile Val
             35                  40                  45

Ala Gly Val Asn Ser Arg Lys Asn Ser Gly Asp Asn Gly Asn Glu Pro
         50                  55                  60

His His Ala Ile Leu Lys Ser Ser Cys Ser Ser Thr Arg Tyr Pro Asp
 65                  70                  75                  80

Leu Cys Phe Ser Ala Ile Ala Ala Val Pro Glu Ala Ser Lys Lys Val
                 85                  90                  95

Thr Ser Gln Lys Asp Val Ile Glu Met Ser Leu Asn Ile Thr Thr Thr
            100                 105                 110

Ala Val Glu His Asn Tyr Phe Gly Ile Gln Lys Leu Leu Lys Arg Thr
            115                 120                 125

Asn Leu Thr Lys Arg Glu Lys Val Ala Leu His Asp Cys Leu Glu Thr
        130                 135                 140

Ile Asp Glu Thr Leu Asp Glu Leu His Lys Ala Val Glu Asp Leu Glu
145                 150                 155                 160

Glu Tyr Pro Asn Lys Lys Ser Leu Ser Gln His Ala Asp Asp Leu Lys
                165                 170                 175

Thr Leu Met Ser Ala Ala Met Thr Asn Gln Gly Thr Cys Leu Asp Gly
            180                 185                 190

Phe Ser His Asp Asp Ala Asn Lys His Val Arg Asp Ala Leu Ser Asp
        195                 200                 205

Gly Gln Val His Val Glu Lys Met Cys Ser Asn Ala Leu Ala Met Ile
    210                 215                 220

Lys Asn Met Thr Asp Thr Asp Met Met Ile Met Arg Thr Ser Asn Asn
225                 230                 235                 240

Arg Lys Leu Ile Glu Glu Thr Ser Thr Val Asp Gly Trp Pro Ala Trp
                245                 250                 255

Leu Ser Thr Gly Asp Arg Arg Leu Leu Gln Ser Ser Val Thr Pro
            260                 265                 270

Asn Val Val Ala Ala Asp Gly Ser Gly Asn Phe Lys Thr Val Ala
        275                 280                 285

Ala Ser Val Ala Ala Pro Gln Gly Gly Thr Lys Arg Tyr Ile Ile
    290                 295                 300

Arg Ile Lys Ala Gly Val Tyr Arg Glu Asn Val Glu Val Thr Lys Lys
305                 310                 315                 320

His Lys Asn Ile Met Phe Ile Gly Asp Gly Arg Thr Arg Thr Ile Ile
                325                 330                 335
```

```
Thr Gly Ser Arg Asn Val Val Asp Gly Ser Thr Thr Phe Lys Ser Ala
        340                 345                 350
Thr Val Ala Val Val Gly Glu Gly Phe Leu Ala Arg Asp Ile Thr Phe
            355                 360                 365
Gln Asn Thr Ala Gly Pro Ser Lys His Gln Ala Val Ala Leu Arg Val
        370                 375                 380
Gly Ala Asp Leu Ser Ala Phe Tyr Asn Cys Asp Met Leu Ala Tyr Gln
385                 390                 395                 400
Asp Thr Leu Tyr Val His Ser Asn Arg Gln Phe Phe Val Asn Cys Leu
            405                 410                 415
Ile Ala Gly Thr Val Asp Phe Ile Phe Gly Asn Ala Ala Ala Val Leu
        420                 425                 430
Gln Asn Cys Asp Ile His Ala Arg Lys Pro Asn Ser Gly Gln Lys Asn
        435                 440                 445
Met Val Thr Ala Gln Gly Arg Ala Asp Pro Asn Gln Asn Thr Gly Ile
        450                 455                 460
Val Ile Gln Lys Ser Arg Ile Gly Ala Thr Ser Asp Leu Lys Pro Val
465                 470                 475                 480
Gln Gly Ser Phe Pro Thr Tyr Leu Gly Arg Pro Trp Lys Glu Tyr Ser
            485                 490                 495
Arg Thr Val Ile Met Gln Ser Ser Ile Thr Asp Val Ile His Pro Ala
            500                 505                 510
Gly Trp His Glu Trp Asp Gly Asn Phe Ala Leu Asn Thr Leu Phe Tyr
        515                 520                 525
Gly Glu His Gln Asn Ala Gly Ala Gly Thr Ser Gly Arg Val
        530                 535                 540
Lys Trp Lys Gly Phe Arg Val Ile Thr Ser Ala Thr Glu Ala Gln Ala
545                 550                 555                 560
Phe Thr Pro Gly Ser Phe Ile Ala Gly Ser Ser Trp Leu Gly Ser Thr
                565                 570                 575
Gly Phe Pro Phe Ser Leu Gly Leu
            580

<210> SEQ ID NO 3
<211> LENGTH: 1323
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
gtagcaatgc gcttgctatg atcaagaaca tgactgacac tgacatgatg atcatgagga      60
cttcaaacaa caggaagctg atagaggaga ccagtacggt tgatgggtgg ccggcgtggc     120
tgtccaccgg agacaggagg ctgttgcagt cctcgtcggt gacaccgaac gtggtggtgg     180
cagcagatgg cagcggaaac tttaagacgg tggcggcagc ggtggcggcg gctcctcagg     240
gaggcactaa gcggtatatt attaggatta aagccggtgt ttatcgggaa atgttgaggs     300
tgacaaagaa gcataaaaat ataatgttca tcggtgacgg gaggactaga actatcatca     360
caggaagtag aaatgtggtt gatgaagca caactttcaa gtctgctaca gttgctgttg     420
ttggtgaagg attcttggcc cgagacatta cattccaaaa cacagccggc ccctcaaagc     480
accaggcggt ggcactacga gtgggagctg acctttcagc attttacaat tgcgatatgt     540
tagcttacca agacacactc tacgtccact cgaaccgcca gttcttgtg aactgcttaa      600
```

-continued

| | |
|---|---|
| ttgctggcac ggttgatttt attttttggta acgctgcagc cgtgttacaa aattgtgaca | 660 |
| tccatgcacg aaagcccaat tccggccaaa aaaatatggt cacagcccaa ggcagggctg | 720 |
| accctaacca aaacaccggc attgtcattc aaaaatctag gattggtgcc acctccgatt | 780 |
| taaaaccggt tcagggtagt ttcccgacgt acctcggcag gccctggaag gagtactcga | 840 |
| ggacggtgat catgcagtca tcgattactg acgtgatcca ccctgccggg tggcacgagt | 900 |
| gggatggtaa cttcgcgttg aacacattgt tttacggaga gcatcagaac gccggagccg | 960 |
| gtgccggaac ttcagggaga gtgaaatgga agggatttag ggttattaca agtgctaccg | 1020 |
| aggctcaagc ttttactcct ggaagcttca ttgctggtag tagctggctg ggctccactg | 1080 |
| gtttcccatt ctcccttggt ttgtaatatt cactaggagt tttaattaat atgttttgta | 1140 |
| ttagtggatc cataggtctc tggtctttca atttgtaata tttgattgag cgtgtcttat | 1200 |
| tcgtggcttc gatttcacaa atactattgt gtgattaaca agaaataaaa tagcatggga | 1260 |
| agaataataa tttccggctt ctttaaaaaa aaaaaaaaaa aaaaaaaaa aaaaaaaaaa | 1320 |
| aaa | 1323 |

<210> SEQ ID NO 4
<211> LENGTH: 1975
<212> TYPE: DNA
<213> ORGANISM: Artificial Sequence
<220> FEATURE:
<223> OTHER INFORMATION: Description of Artificial Sequence: Synthetic
       Oligonucleotide

<400> SEQUENCE: 4

| | |
|---|---|
| cttttgttct ctcttatcga gaaaaaaaat gacccgcata aaagaattct tcacaaaact | 60 |
| ttctgaatct tctaccaacc aaaacatttc caatattccc aagaaaaaaa agaaactatt | 120 |
| cttagctctt tttgcaacgc tactcgttgt cgctgccgta atcggcattg tcgccggagt | 180 |
| gaactcaaga aaaaactccg gcgacaacgg caacgagcct catcatgcta tcctcaaatc | 240 |
| atcatgtagc agcacaaggt acccggactt atgcttttcg gctattgctg ccgttccaga | 300 |
| ggcctccaaa aaggtgacaa gccaaaagga cgttattgag atgtccttaa acatcacaac | 360 |
| aacagccgtg gaacacaact acttcgggat tcagaagctc ttgaagagaa cgaatctcac | 420 |
| caaacgggaa aaggttgctc tccatgactg tcttgagacg atcgatgaga ctcttgatga | 480 |
| gttacacaaa gccgtcgagg atcttgagga gtacccgaac aagaaatctt tatcacagca | 540 |
| tgcggatgat ctcaaaaccc taatgagtgc cgcgatgacc aatcagggga cgtgtcttga | 600 |
| tgggttctct catgatgatg ctaataagca cgtgcgggat gcgttgtcag acggccaggt | 660 |
| tcatgttgag aagatgtgta gcaatgcgct tgctatgatc aagaacatga ctgacactga | 720 |
| catgatgatc atgaggactt caaacaacag gaagctgata gaggagacca gtacggttga | 780 |
| tgggtggccg gcgtggctgt ccaccggaga caggaggctg ttgcagtcct cgtcggtgac | 840 |
| accgaacgtg gtggtggcag cagatggcag cggaaacttt aagacggtgg cggcatcggt | 900 |
| ggcggcggct cctcagggag gcactaagcg gtatattatt aggattaaag ccggtgttta | 960 |
| tcgggaaaat gttgaggtga caaagaagca taaaaatata atgttcatcg gtgacgggag | 1020 |
| gactagaact atcatcacag ggagtagaaa tgtggttgat ggaagcacaa ctttcaagtc | 1080 |
| tgctacagtt gctgttgttg gtgaaggatt cttggcccga gacattacat tccaaaacac | 1140 |
| agccggcccc tcaaagcacc aggcggtggc actacgagtg ggagctgacc tttcagcatt | 1200 |
| ttacaattgc gatatgttag cttaccaaga cacactctac gtccactcga accgccagtt | 1260 |

```
                                                       -continued ctttgtgaac tgcttaattg ctggcacggt tgattttatt tttggtaacg ctgcagccgt   1320
gttacaaaat tgtgacatcc atgcacgaaa gcccaattcc ggccaaaaaa atatggtcac   1380
agcccaaggc agggctgacc ctaaccaaaa caccggcatt gtcattcaaa aatctaggat   1440
tggtgccacc tccgatttaa aaccggttca gggtagtttc ccgacgtacc tcggcaggcc   1500
ctggaaggag tactcgagga cggtgatcat gcagtcatcg attactgacg tgatccaccc   1560
tgccgggtgg cacgagtggg atggtaactt cgcgttgaac acattgtttt acggagagca   1620
tcagaacgcc ggagccggtg ccggaacttc agggagagtt aaatggaagg gatttagggt   1680
tattacaagt gctaccgagg ctcaagcttt tactcctgga agcttcattg ctggtagtag   1740
ctggctgggc tccactggtt tcccattctc ccttggtttg taatattcac taggagtttt   1800
aattaatatg ttttgtatta gtggatccat aggtctctgg tctttcaatt tgtaatattt   1860
gattgagcgt gtcttattcg tggcttcgat ttcacaaata ctattgtgtg attaacaaga   1920
aataaaatag catgggaaga ataataattt ccggcttctt taaattaaaa aaaaa       1975
```

COMPOSITION COMPRISING PECTIN METHYL ESTERASE AND TWO SUBSTRATES

CROSS-REFERENCE TO RELATED APPLICATIONS

This application claims priority to PCT Application No. PCT/IB98/00673, filed Apr. 24, 1998, which claims priority to GB Application No. 9708278.8, filed Apr. 24, 1997.

FIELD OF THE INVENTION

The present invention relates to a composition. In particular, the present invention relates to a composition for use as or in the preparation of a foodstuff. More in particular, the present invention relates to a composition for use as or in the preparation of a foodstuff comprising or made from a pectin or a pectin derivative.

BACKGROUND OF THE INVENTION

Pectin is an important commodity in today's industry. For example, it can be used in the food industry as a thickening or gelling agent, such as in the preparation of jams.

Pectin is a structural polysaccharide commonly found in the form of protopectin in plant cell walls. The backbone of pectin comprises α-1-4 linked galacturonic acid residues which are interrupted with a small number of 1,2 linked α-L-rhamnose units. In addition, pectin comprises highly branched regions with an almost alternating rhamno-galacturonan chain. These highly branched regions also contain other sugar units (such as D-galactose, L-arabinose and xylose) attached by glycosidic linkages to the C3 or C4 atoms of the rhamnose units or the C2 or C3 atoms of the galacturoric acid units. The long chains of α-1-4 linked galacruronic acid residues are commonly referred to as "smooth" regions, whereas the highly branched regions are commonly referred to as the "hairy regions".

Some of the carboxyl groups of the galacturonic residues are esterified (e.g. the carboxyl groups are methylated). Typically esterification of the carboxyl groups occurs after polymerisation of the galacturonic acid residues. However, it is extremely rare for all of the carboxyl groups to be esterified (e.g. methylated). Usually, the degree of esterification will vary from 0–90%. If 50% or more of the carboxyl groups are esterified then the resultant pectin is referred to as a "high ester pectin" ("HE pectin" for short) or a "high methoxyl pectin". If less than 50% of the carboxyl groups are esterifled then the resultant pectin is referred to as a "low ester pectin" ("LE pectin" for short) or a "low methoxyl pectin". If 50% of the carboxyl groups are esterifled then the resultant pectin is referred to as a "medium ester pectin" ("ME pectin" for short) or a "medium methoxyl pectin". If the pectin does not contain any—or only a few—esterified groups it is usually referred to as pectic acid.

The structure of the pectin, in particular the degree of esterification (e.g. methylation), dictates many of the resultant physical and/or chemical properties of the pectin. For example, pectin gelation depends on the chemical nature of the pectin, especially the degree of esterification. In addition, however, pectin gelation also depends on the to soluble-solids content, the pH and calcium ion concentration. With respect to the latter, it is believed that the calcium ions form complexes with free carboxyl groups, particularly those on a LE pectin.

Pectic enzymes are classified according to their mode of attack on the galacturonan part. of the pectin molecule. A review of some pectic enzymes has been prepared by Pilnik and Voragen (Food Enzymology, Ed.: P. F. Fox; Elsevier; (1991); pp: 303–337). In particular, pectin methylesterases (EC 3.1.1.11), otherwise referred to as PMEs, de-esterify HE pectins to LE pectins or pectic acids. In contrast, and by way of example. pectin depolymerases split the glycosidic linkages between galacturonosyl methylester residues.

In more detail, PME activity produces free carboxyl groups and free methanol. The increase in free carboxyl groups can be easily monitored by automatic titration. In this regard, earlier studies have shown that some PMEs de-esterify pectins in a random manner, in the sense that they de-esterify any of the esterified (e.g. methylated) galacturonic acid residues on one or more than one of the pectin chains. Examples of PMEs that randomly de-esterify pectins may be obtained from fungal sources such as *Aspergillus aculearus* (see WO 94/25575) and *Aspergillus japonicus* (Ishii et al 1980 J Food Sci 44 pp 611–14). Baron et al (1980 Lebensm. Wiss. M-Technol 13 pp 330–333) apparently have isolated a rungs PME term *Aspergillus niger*. This fungal PME is reported to have a molecular weight of 39000 D, an isoelectric point of 3.9, an optimum pH of 4.5 and a $K_m$ value (mg/ml) of 3.

In contrast, some PMEs are known to de-esterify pectins in a block-wise manner, in the sense that it is believed they attack pectins either at non-reducing ends or next to free carboxyl groups and then proceed along the pectin molecules by a single-chain mechanism, thereby creating blocks of un-esterified galacruronic acid units which can be calcium sensitive. Examples of such enzymes that block-wise enzymatically de-esterify pectin are plant PMEs. Up to 12 isoforms of PME have been suggested to exist in citrus (Pilnik W. and Voragen A. G. J. (Food Enzymology (Ed.: P. F. Fox); Elsevier; (1991); pp: 303–337). These isoforms have different properties.

Random or blockwise distribution of free carboxyl groups can be distinguished by high performance ion exchange chromatography (Schols et al Food Hydrocolloids 1989 6 pp 115–121). These tests are often used to check for undesirable, residual PME activity in citrus juices after pasteurisation because residual PME can cause, what is called, "cloud loss" in orange juice in addition to a build up of methanol in the juice.

PME substrates, such as pectins obtained from natural plant sources, are generally in the form of a high ester pectin having a DE of about 70%. Sugar must be added to extracts containing these high ester PME substrates to provide sufficient soluble solids to induce gelling. Usually a minimum of 55% soluble solids is required. Syneresis tends to occur more frequently when the percentage soluble solids is less than 55%. When syneresis does occur, expensive additives must be used to induce gelling.

Versteeg er al (J Food Sci 45 (1980) pp 969–971) apparently have isolated a PME from orange. This plant PME is reported to occur in multiple isoforms of differing properties. Isoform I has a molecular weight of 36000 D, an isoelectric point of 10.0, an optimum pH of 7.6 and a $K_m$ value (mg/ml) of 0.083. Isoform II has a molecular weight of 36200 D, an isoelectric point of 11.0, an optimum pH of 8.8 and a $K_m$ value (mg/ml) of 0.0046. Isoform III (HMW-PE) has a molecular weight of 54000 D, an isoelectric point of 10.2, an optimum pH of 8 and a $K_m$ value (mg/ml) of 0.041. However, to date there has been very limited sequence data for such PMEs.

According to Pilnik and Voragen (ibid), PMEs may be found ia a number of other higher plants, such as apple, apricot, avocado, banana, berries, lime, grapefruit, mandarin, cherries, currants, grapes, mango, papaya, passion fruit, peach, pear, plums, beans, carrots, cauliflower, cucumber, leek, onions, pea, potato, radish and tomato. However, likewise, to date there has been very limited sequence data for such PMEs.

A plant PME has been reported in WO-A-97/03574 (the contents of which are incorporated herein by reference). This PME has the following characteristics: a molecular weight of from about 36 kD to about 64 kD; a pH optimum of pH 7–8 when measured with 0.5% lime pectin in 0.15 M NaCl; a temperature optimum of at least 50° C.; a temperature stability in the range of from 10°—at least 40° C.; a $K_m$ value of 0.07%; an activity maximum at levels of about 0.25 M NaCl; an activity maximum at levels of about 0.2 M $Na_2SO_4$; and an activity maximum at levels of about 0.3 M $NaNO_3$.

Another PME has been reported in WO 97/31102 (the contents of which are incorporated herein by reference).

PMEs have important uses in industry. For example, they can be used in or as sequestering agents for calcium ions. In this regard, and according to Pilnik and Voragen (ibid), cattle feed can be prepared by adding a slurry of calcium hydroxide to citrus peels after juice extraction. After the addition, the high pH and the calcium ions activate any native PME in the peel causing rapid de-esterification of the pectin and calcium pectate coagulation occurs. Bound liquid phase is released and is easily pressed out so that only a fraction or the original water content needs to be removed by expensive thernal drying. The press liquor is then used as animal feed.

As indicated above, a PME has been obtained from Aspergillus aculeatus (WO 94/25575). Apparently, this PME can be used to improve the firmness of a pectin-containing material, or to de-methylate pectin, or to increase the viscosity of a pectin-containing material.

It has also become common to use PME in the preparation of foodstuffs prepared from fruit or vegetable materials containing pectin—such as jams or preservatives. For example, WO-A-94/25575 further reports on the preparation of orange marmalade and tomato paste using PME obtained from Aspergillus aculeatus.

JP-A-63/209553 discloses gels which are obtained by the action of pectin methylesterase, in the presence of a polyvalent metal ion, on a pectic polysaccharide containing as the main component a high-methoxyl poly α-1,4-D-galacturonide chain and a process for their production.

Pilnik and Voragen (ibid) list uses of endogenous PMEs which include their addition to fruit juices to reduce the viscosity of the juice if it contains too much pectin derived from the fruit, their addition as pectinase solutions to the gas bubbles in the albedo of citrus fruit that has been heated to a core temperature of 20° C. to 40° C. in order to facilitate removal of peel and other membrane from intact juice segments (U.S. Pat. No. 4,284,651), and their use in protecting and improving the texture and firmness of several processed fruits and vegetables such as apple (Wiley & Lee 1970 Food Technol 24 1168–70), canned tomatoes (Hsu et al 1965 J Food Sci 30 pp 583–588) and potatoes (Bartolome & Hoff 1972 J Agric Food Chem 20 pp 262–266).

Glahn and Rolin (1994 Food Ingredients Europe, Conf Proceedings pp 252–256) report on the hypothetical application of the industrial "GENU pectin type YM-100" for interacting with sour milk beverages. No details are presented at all on how GENU pectin type YM-100 is prepared.

EP-A-0664300 discloses a chemical fractionation method for preparing calcium sensitive pectin. This calcium sensitive pectin is said to be advantageous tor the food industry.

Thus, pectins and de-esterified pectins, in addition to PMEs, have an industrial importance.

SUMMARY OF THE INVENTION

We have now found that a benefit derived from use of a PME in the preparation of, for example, a foodstuff will depend to some extent on the quality and quantity and type of the PME used and on the quality and quantity and tvpe of the PME substrates—in particular pectin—that may be present in the material used to prepare the foodstuff. For example, if the substrate is a fruit material or a vegetable material then the amount and/or structure of natural pectin in that substrate will be different for different types of fruit material or vegetable material. This is also borne out by the data presented in WO-A-94/25575, especially FIG. 7 where it is clear to see that its PME system is not ideal.

DETAILED DESCRIPTION OF THE INVENTION

Figure 1:
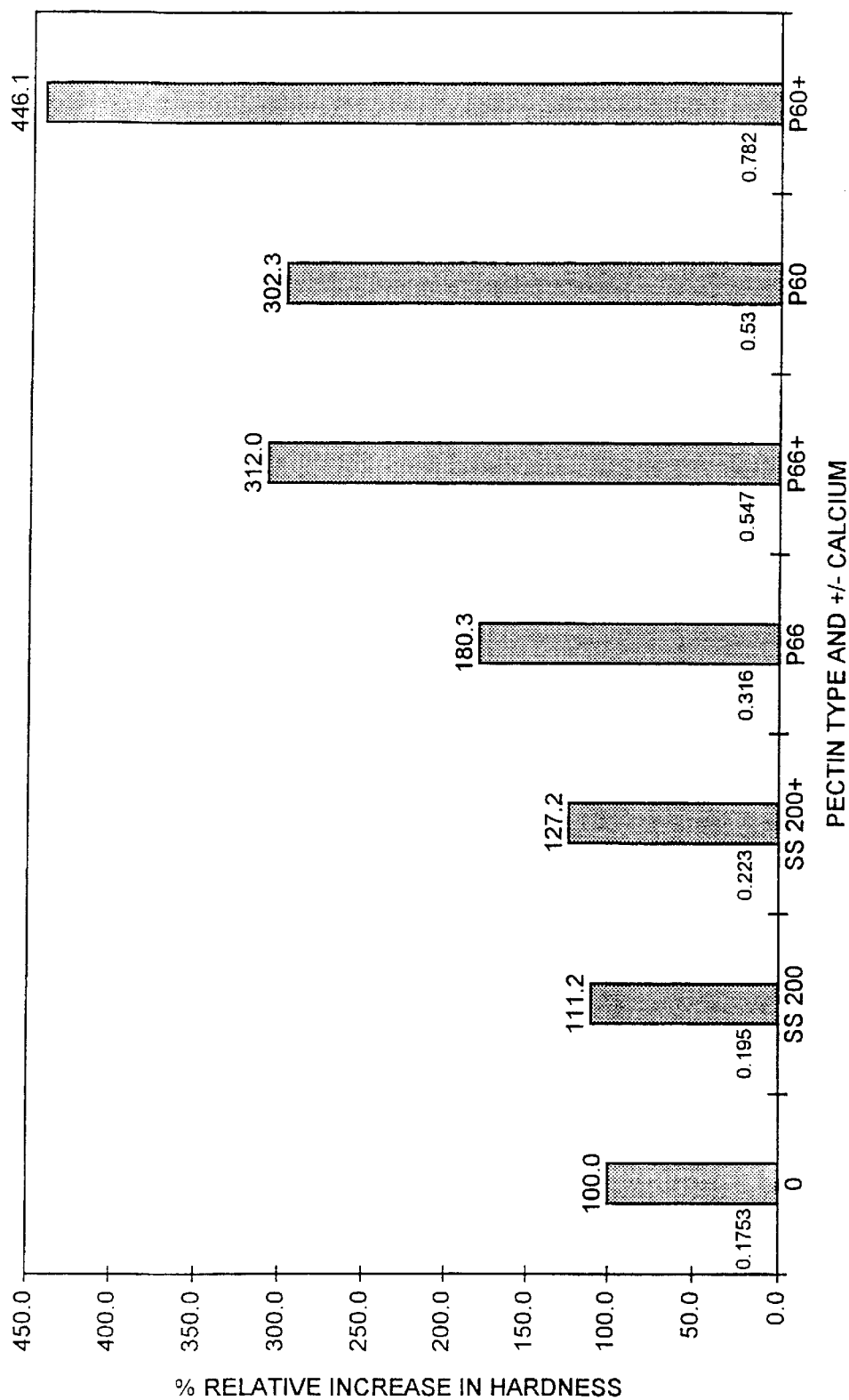
FIG. 1 is a bar chart showing the effect of PPME modification, added pectin and +/− calcium.

According to the present invention we have now found that addition of an additional PME substrate enables one to derive even more benefit from the use of a PME in the preparation of, for example, a foodstuff.

In this regard, addition of an additional PME substrate will overcome any problems associated with differing quantities and qualities of PME substrates that may be found in materials used in the preparation of, for example, foodstuffs.

According to a first aspect of the present invention there is provided a composition comprising a pectin methyl esterase ("PME"); a first PME substrate; and a second PME substrate; wherein neither the first PivIE substrate nor the second PME substrate originates in situ from the other.

According to a second aspect of the present invention there is provided a method of preparing a composition, the method comprising forming a mixture of a PME; a first PME substrate; and a second PME substrate; wherein neither the first PME substrate nor the second PME substrate originates in situ from the other.

According to a third aspect of the present invention there is provided a process comprising adding to a first PME substrate, PME and a second PME substrate; wherein neither the first PME substrate nor the second PME substrate originates in situ from the other.

According to a fourth aspect of the present invention there is provided a foodstuff comprising or prepared from or by the other aspects of the present invention.

According to a fifth aspect of the present invention there is also provided a composition made from a pectin methyl esterase ("PME"); a first PME substrate; and a second PME substrate; wherein neither the first PME substrate nor the second PME substrate originates in situ from the other.

According to a sixth aspect of the present invention there is provided a process of un imparting stability to a reaction medium comprising a first PME substrate, the process comprising adding at least PME and a second PME substrate; wherein neither the first PME substrate nor the second PME substrate originates in situ from the other.

Thus, in its broadest sense, the present invention provides a composition comprising a PME; a first PME substrate; and a second PME substrate; wherein neither the first PME substrate nor the second PME substrate originates in situ from the other.

With the present invention, neither the first PME substrate nor the second PME substrate originates in situ from the other. The term "neither the first PME substrate nor the second PME substrate originates in situ from the other" means that the first PME substrate does not originate in situ from the second PME substrate and/or the second PME substrate does not originate from the first PME substrate. Hence, with the present invention, the first PME substrate has not been derived in situ from the second PME substrate and vice versa. Thus, for example, the composition of the present invention does not encompass just a quantity of a first PME substrate wherein a portion of that PME substrate has been partially modified by a PME enzyme. In contrast, a second PME substrate must be also present—wherein that second PME substrate has not originated in situ from the first PME substrate.

With the composition of the present invention, there can be present additional, different PME substrate(s).

The PME substrates in or for the composition of the present invention may be obtainable from different sources and/or may be of different chemical composition.

Likewise, with the composition of the present invention, there can be present additional, different PME enzyme(s).

If there is more than one PME present, then the PME enzymes may be obtainable from different sources and/or may be of different composition and/or may have a different reactivity profile (e.g. different pH optimum and/or different temperature optimum).

With the present invention, the PME enzyme may de-esterifu the PME substrates in a random manner or in a block-wise manner. If there is more than one PME, then each PME is independently selected from a PME that can de-esterify the PME substrate(s) in a random manner or a PME that can de-esterify the PME substrate(s) in a block-wise manner.

In one preferred embodiment, the (or at least one) PME enzyme de-esterifies the PME substrate(s) in a block-wise manner.

If there is more than one PME, then each PME is independently selected from a PME enzyme that is sensitive to sodium ions (Na-sensitive) or a PME enzyme that is insensitive to sodium ions (Na-insensitive). In one preferred embodiment, the (or at least one) PME enzyme is a PME enzyme that is Na-sensitive.

The PME may be obtainable from natural sources or even obtained from natural sources or it may be chemically synthesised.

For example, the PME may be obtainable from a fungus, such as by way of example a PME of fungal origin (i.e. a PME that has been obtained from a fungus).

Alternatively, the PME may be obtainabie from a bacterium, such as by way of example a PME of bacterial origin (i.e. a PME that has been obtained from a bacterium).

Alternatively, the PME may be obtainable from a plant, such as by way of example a PME of plant origin (i.e. a PME that has been obtained from a plant).

In one preferred embodiment, the PME is prepared by use of recombinant DNA techniques.

For example, the PME can be a recombinant PME as disclosed in WO-A-97/03574 or the PME disclosed in either WO-A-94/25575 or WO-A-97/31102 as well as variants, derivatives or homologues of the sequences disclosed in those patent applications.

In one preferred embodiment the PME is the recombinant PME of WO-A-97/03574 (the contents of which are incorporated herein by reference)—such as the PME of SEQ.I.D. No. 1 or SEQ.I.D. No. 2 (which are coded by the nucleotide sequences presented as SEQ.I.D. No. 3 and SEQ.I.D. No. 4 respectively) or a variant, derivative or homologue thereof; and/or the PME of WO-A-94/25575 (the contents of which are incorporated herein by reference), or a variant, derivative or homologue thereof.

The terms "variant", "homologue" or "fragment" in relation to the recombinant enzyme of the present invention include any substitution of, variation of, modification of, replacement of, deletion of or addition of one (or more) amino acid from or to the sequence providing the resultant amino acid sequence has PME activity, preferably having at least the same activity of a recombinant enzyme comprising any one or more of the sequences shown as SEQ I.D. No.s 1 and 2. In particular, the term "homologue" covers homology with respect to structure and/or function providing the resultant recombinant enzyme has PME activity. With respect to sequence homology (i.e. similarity), preferably there is at least 75%, more preferably at least 85%, more preferably at least 90% homology to the sequences shown in the attached sequence listings. More preferably there is at least 95%, more preferably at least 98%, homology to the sequences shown in the attached sequence listings.

The terms "variant", "homologue" or "fragment" in relation to the nucleotide sequence coding for the recombinant enzyme of the present invention include any substitution of, variation of, modification of, replacement of, deletion of or addition of one (or more) nucleic acid from or to the sequence providing the resultant nucleotide sequence codes for a recombinant enzyme having PME activity, preferably having at least the same activity of a recombinant enzyme comrprising any one or more of the sequences shown as SEQ I.D. No.s 1 and 2. In particular, the term "homologue" covers homology with respect to structure and/or function providing the resultant nucleotide sequence codes for a recombinant enzyme having PME activity. With respect to sequence homology (i.e. similarity), preferably there is at least 75%, more preferably at least 85%, more preferably at least 90% homology. More preferably there is at least 95%, more preferably at least 98%, homology.

The above terms are synonymous with allelic variations of the sequences.

In a preferred embodiment, at least one of the PME substrates is pectin or is a substrate that is derivable from or derived from pectin (eg. a pectin derivative).

The term "derived from pectin" includes derivatised pectin, degraded (such as partially degraded) pectin and modified pectin. An example of a modified pectin is pectin that has been prior treated with an enzyme such as a PME. An example of a pectin derivative is pectin that has been chemically treated—eg. amidated.

Preferably, each of the first PME substrate and the second PME substrate is independently selected from pectin, a substrate that is derivable from pectin, or a substrate that is derived from pectin.

In one preferred embodiment, each of the first PME substrate and the second PME substrate is pectin.

In another preferred embodiment, either the first PME substrate or the second PME substrate is a modified pectin—in particular an enzymatically modified pectin, preferably a PME treated pectin.

In a preferred embodiment, the second PME substrate is such a modified pectin.

In another preferred embodiment, each of the first PME substrate and the second PME substrate is such a modified pectin.

Preferably, the first PME substrate is present within (i.e. in situ) a plant or a plant material. The plant may be a transgenic plant, such as a plant that has been genetically engineered to produce different levels and/or types of pectin. Likewise, the plant material may be obtained from a transgenic plant, such as a plant that has been genetically engineered to produce different levels and/or types of pectin.

The plant or plant material may be or may be derived from a vegetable, a fruit, or other type of pectin containing or producing plant.

Preferably, the plant material is a vegetable material and/or a fruit material.

Preferably, the vegetable material and/or the fruit material is a mash.

The first PME substrate and/or the second PME substrate can be any one or more of a low ester pectin, a medium ester pectin or a high ester pectin.

Preferably, the second PME substrate is a low ester pectin, a medium ester pectin or a high ester pectin. A Protocol for determining the degree of esterification of the PME substrate may be found on page 58 of WO-A-97/03574 (the contents of which are incorporated herein by reference). For ease of reference, this Protocol is recited in the Examples section (infra).

In one preferred embodiment, the second PME substrate is a high ester pectin.

For the present invention the first PME subscrare and the second PME substrate are independently selected from a PME substrate that is sensitive to calcium ions (Ca-sensitive) or a PME substrate that is insensitive to calcium ions (Ca-insensitive). A Protocol for determining calcium sensitivity may be found on page 57 of WO-A-97/03574 (the contents of which are incorporated herein by reference). For ease of reference, this Protocol is recited in the Examples section (infra).

In one preferred embodiment, the second PME substrate is Ca-sensitive.

Preferably, the second PME substrate is added to the first PME substrate. Here, the term "added to" includes physically adding the second PME substrate to the first PME substrate and vice versa.

The PME may be added at the same time as the second PME substrate, or before the addition of the second PME substrate or after the addition of the second PME substrate.

Hence, the present invention encompasses at least the following possibilities: adding PME to the first PME substrate and at the same time as the second PME substrate; adding PME to the second PME substrate and at the same time as the first PME substrate; adding the second PME substrate to PME and at the same tune as the first PME substrate, adding PME and the first PME substrate and the second PME substrate at the same time to a reaction vessel; incubating the first PME substrate with PME prior to addition to the second PME substrate; incubating the second PME substrate with PME prior to addition to the first PME substrate; incubating the first PME substrate with PME prior to addition to the second PME substrate and then adding more PME (which may be the same or different as the other PME); incubating the second PME substrate with PME prior to addition to the first PME substrate and then adding more PME (which may be the same or different as the other PME); incubating the first PME substrate with PME prior to addition to the second PME substrate and then adding a further PNE substrate (which may be the same or different as the other PME substrates); incubating the second PME substrate with PME prior to addition to the first PME substrate and then adding a further PME substrate (which may be the same or different as the other PME substrates); adding the first PME substrate when incubating with PME to the second PME substrate when incubating with PME (which may be the same or different to the other PME); addition of the first PME substrate after it has been incubated with PME (optionally wherein the reaction has been stopped—such as by application of heat) to the second PME substrate after it has been incubated with PME which may be the same or different to the other PME (optionally wherein the reaction has been stopped—such as by application of heat); as well as any combination thereof.

In a number of embodiments, preferably the present invention comprises any one or more of: adding PME to the first PME substrate and at the same time as the second PME substrate; adding PME to the second PME substrate and at the same time as the first PME substrate; addin g the second PME substrate to PME and at the same time as the first PME substrate; adding PME and the first PME substrate and the second PME substrate at the same time to a reaction vessel; incubating the first PME substrate with PME prior to addition to the second PME substrate; incubating the second PME substrate with PME prior to addition to the firs t PME substrate; incubating the first PME substrate with PME prior to addition to the second PME substrate and then adding more PME (which may be the same or different as the other PME); incubating the second PME substrate with PME prior to addition to the first PME substrate and then adding more PME (which may be the same or different as the other PME); incubating the first PME substrate with PME prior to addition to the second PME substrate and then adding a further PME substrate (which may be the same or different as the other PME substrates); incubating the second PME substrate with PME prior to addition to the first PME substrate and then adding a further PME substrate (which may be the same or different as the other PME substrates), adding the first PME substrate when incubating with PME to the second PME substrate when incubating with PME (which may be the same or different to the other PME).

Thus, in one embodiment, it is possible to prepare a high ester, PME pretreated second PME substrate which could then be added to a first PME substrate. In this regard, it would be possible to exploit different PMEs (such as, but not limited to, recombinant, plant, fungal and bacterial PMEs) to modify the second PME substrate with a view to providing PME substrates with different functionality in a combination system.

Alternatively expressed, this embodiment of the present invention provides a composition comprising a PME; a first PME substrate; and a second PME substrate; wherein neither the first PME substrate nor the second PME substrate originates in situ from the other; and wherein at least the second PME substrate has been PME pre-treated.

In another embodiment, it is possible to add a PME substrate to a high ester, PME pretreated first PME substrate. In this regard, it would be possible to exploit different PMEs (such as, but not limited to, recombinant, plant, fungal and bacterial PMEs) to modif the second PME substrate with a view to providing PME substrates with different functionality in a combination system.

In another embodiment, it is possible to prepare a high ester, PME pretreated second PME substrate which could then be added to a high ester, PME pretreated first PME substrate. In this regard, it would be possible to exploit different PMEs (such as, but not limited to, recombinant, plant, fungal and bacterial PMEs) to modify the second PME substrate with a view to providing PME substrates with different functionality in a combination system.

The composition may comprise one or more other components, such as one or more suitable food ingredients. Typical food ingredients include anv one or more of an acid—such as citric acid—or a sugar—such as sucrose, glucose or invert sugar—or fruit—or other enzymes, preservatives, colourings and other suitable components.

The composition of the present invention can be used in the preparation of a foodstuff. For example, it may be a starting reagent or an intermediate in the preparation of a foodstuff.

Alternatively, the composition of the present invention can be the foodstuff itself.

The term "foodstuff" can include food for human and/or animal consumption. Typical foodstuffs include jams, marmalades, jellies, dairy products (such as milk or cheese), meat products, poultry products, fish products and bakery products. The foodstuff may even be a beverage. The beverage can be a drinking yoghurt, a fruit juice or a beverage comprising whey protein.

The (or any one or more of each) PME may be used in conjunction with other types of enzymes.

Examples of other types of enzymes include other pectinases, pectin depolymerases, poly-galacturonases, pectate lyases, pectin lyases, rhamno-galacruronases, galactanases, cellulases, hermicellulases, endo-β-glucanases, arabinases, acetyl esterases, or pectin releasing enzymes, or combinations thereof.

These other types of enzymes can be added at the same time as the PME or, alternatively, prior to or after the addition of the PME.

In one preferred embodiment the PME is used in conjunction with one or more poly-galacturonases, such as an endo-poly-galacturonase (such as that of WO-A-89/12648, the contents of which are incorporated herein by reference) and/or an exo-poly-galacturonase (such as that of WO-A-94/14966, the contents of which are incorporated herein by reference). This preferred embodiment is of benefit for jam and marmalade manufacture as the resultant treated PME substrates may achieve more controlled calcium sensitivity. As indicated above, the teachings of WO-A-97/03574 provide some useful teachings on how to prepare a suitable PME for use in the present invention by use of recombinant DNA techniques. Some of these teachings are recited below.

In order to express a recombinant PME, the host organsm can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the gene may need to be suitably modified before transformation—such as by removal of introns.

In one embodiment, the host organism can be of the genus Aspergillus, such as *Aspergillus niger*. A transgenic Aspergillus can be prepared by following the teachings of Rambosek. J. and Leach, J. 1987 (Recombinant DNA in filamentous fungi: Progress and Prospects. CRC Crit. Rev. Biotechnol. 6:357–393), Davis R. W. 1994 (Heterologous gene expression and protein secretion in Aspergillus. In: Martinelli S. D., Kinghorn J. R.(Editors) Aspergillus: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong, S. A., Berka R. M. (Editors) Molecular Industrial Mycology. Systems and Applications for Filamentous Fungi. Marcel Dekker Inc. New York 1991. pp 1–29) and Turner G. 1994 (Vectors for genetic manipulation. In: Martinelli S. D., Kinghorn J. R.(Editors) Aspergillus: 50 years on. Progress in industrial microbiology vol 29. Elsevier Amsterdam 1994. pp. 641–666). However, the following commentary provides a summary of those teachings for producing transgenic Aspergillus.

For almost a century, filamentous fungi have been widely used in many types of industry for the production of organic compounds and enzymes.

For example, traditional japanese koji and soy fermentations have used Aspergillus sp. Also, in this century *Aspergillus niger* has been used for production of organic acids particular citric acid and for production of various enzymes for use in industry.

There are two major reasons why filamentous fungi have been so widely used in industry. First filamentous fungi can produce high amounts of extracelluar products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous expression for recombinant PME.

In order to prepare the transgenic Aspergillus, expression constructs are prepared by inserting a requisite nucleotide sequence into a construct designed for expression in filamentous fungi.

Several types of constructs used for heterologous expression have been developed. These constructs can contain a promoter which is active in fungi. Examples of promoters to include a fungal promoter for a highly expressed extracelluar enzyme, such as the glucoamylase promoter or the α-amylase promoter. The nucleotide sequence can be fused to a signal sequence which directs the protein encoded by the nucleotide sequence to be secreted. Usually a signal sequence of fungal origin is used. A terminator active in fungi ends the expression system.

Another type of expression system has been developed in fungi where the nucleotide sequence can be fused to a smaller or a larger part of a fungal gene encoding a stable protein. This can stabilize the protein encoded by the nucleotide sequence. In such a system a cleavage site, recognized by a specific protease, can be introduced between the fungal protein and the protein encoded by the nucleotide sequence, so the produced fusion protein can be cleaved at this position by the specific protease thus liberating the protein encoded by the nucleotide sequence. By way of example, one can introduce a site which is recognized by a KEX-2 like peptidase found in at least some Aspergilli. Such a fusion leads to cleavage in vivo resulting in protection of the expressed product and not a larger fusion protein.

Heterologous expression in Aspergillus has been reported for several genes coding for bacterial, fungal, vertebrate and plant proteins. The proteins can be deposited intracellularly if the nucleotide sequence is not fused to a signal sequence. Such proteins will accumulate in the cytoplasm and will usually not be glycosylated which can be an advantage for some bacterial proteins. If the nucleotide sequence is equipped with a signal sequence the protein will accumulate extracelluarly.

With regard to product stability and host strain modifications, some heterologous proteins are not very stable when they are secreted into the culture fluid of fungi. Most fungi produce several extracelluar proteases which degrade heterologous proteins. To avoid this problem special fungal strains with reduced protease production have been used as host for heterologous production.

For the transformation of filamentous fungi, several transformation protocols have been developed for many filamentous fungi (Ballance 1991, ibid). Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A commonly used transformation marker is the amdS gene of A. nidulans which in high copy number allows the fungus to grow with acrylamide as the sole nitrogen source.

In another embodiment the transgenic organism can be a yeast. In this regard, yeast have also been widely used as a vehicle for heterologous gene expression. The species Saccharomyces cerevisiae has a long history of industrial use, including its use for heterologous gene expression. Expression of heterologous genes in Saccharomyces cerevisiae has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons Saccharomyces cerevisiae is well suited for heterologous gene expression. First, it is non-pathogenic to humans and it is incapable of producing certain endotoxins. Second, it has a long history of safe use following centuries of comtercial exploitation for various purposes. This has led to wide public acceptability. Third, the extensive commercial use and research devoted to the organism has resulted in a wealth of knowledge about the genetics and physiology as well as large-scale fermentation characteristics of Saccharomyces cerevisiae.

A review of the principles of heterologous gene expression in Saccharomyces cerevisiae and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academnic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encodina the SUC2 signal peptide, is used. A terminator active in yeast ends the expression system.

For the transformation of yeast several transformation protocols have been developed. For example, a transgenic Saccharomyces can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. In this regard, the art is replete with references for preparing transgenic plants. Two documents that provide some background commentary on the types of techniques that may be employed to prepare transgenic plants are EP-B-0470145 and CA-A-2006454—some of which commentary is presented below.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and indirect introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

A suitable transformation svstem for a plant may comprise one vector, but it can comprise two vectors. In the case of two vectors, the vector system is normally referred to as a binary vector system. Binary vector systems are described in further detail in Gynheung An et al. (1980), Binary Vectors, Plant Molecular Biology Manual A3, 1–19.

One extensively employed system for transformation of plant cells with a given promoter or nucleotide sequence or construct is based on the use of a Ti plasmid from Agrobacterium tumefaciens or a Ri plasmid from Agrobacterium rhizogenes as described in An et al. (1986), Plant Physiol. 81, 301–305 and Butcher D. N. et al. (1980), Tissue Culture Methods for Plant Pathologists, eds.: D. S. Ingrams and J. P. Helgeson, 203–208.

Several different Ti and Ri plasmids have been constructed which are suitable for the construction of the plant or plant cell constructs described above. A non-limiting example of such a Ti plasmid is pGV3850.

The nucleotide sequence or construct should preferably be inserted into the Ti-plasmid between the terminal sequences of the T-DNA or adjacent a T-DNA sequence so as to avoid disruption of the sequences inmrediately surrounding the T-DNA borders, as at least one of these regions appear to be essential for insertion of modified T-DNA into the plant genome.

As will be understood from the above explanation, if the organism is a plant, then the vector system is preferably one which contains the sequences necessar to infect the plani (e.g. the vir region) and at least one border part of a T-DNA secuence, the border part being located on the same vector as the genetic construct. Preferably, the vector system is an Agrobacterium tumefaciens Ti-plasmid or an Agrobacterium rhizogenes Ri-plasmid or a derivative thereof, as these plasmids are well-known and widely employed in the construction of transgenic plants, many vector systems exist which are based on these plasmids or derivatives thereof.

In the construction of a transgenic plant the nucleotide sequence may be first constructed in a microorganism in which the vector can replicate and which is easy to manipulate before insertion into the plant. An example of a useful microorganism is *E. coli.*, but other microorganisms having the above properties may be used. When a vector of a vector system as defined above has been constructed in *E. coli.* it is transferred, if necessary, into a suitable Agrobacterium strain, e.g. *Agrobacterium tumefaciens.* The Ti-plasmid harbouring the nucleotide sequence or construct is thus preferably transferred into a suitable Agrobacterium strain, e.g. *A. tumefaciens*, so as to obtain an Agrobacrerium cell harbouring the nucleotide sequence, which DNA is subsequently transferred into the plant cell to be modified.

As reported in CA-A-2006454, a large amount of cloning vectors are available which contain a replication system in *E. coli* and a marker which allows a selection of the transformed cells. The vectors contain for example pBR 322, the pUC series, the M13 mp series, pACYC 184 etc.

In this way, the nucleotide sequence can be introduced into a suitable restriction position in the vector. The contained plasmid is used for the transformation in *E.coli.* The *E.coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After each introduction method of the desired promoter or construct or nucleotide sequence in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasuid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al., EMBO J. (1985) 4:277–284.

Direct infection of plant tissues by Agrobacterium is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be done on a certain part or tissue of the plant, i.e. on a part of a leaf, a root, a stem or another part of the plant.

Typically, with direct infection of plant tissues by Agrobacrerium carrying the promoter and/or the GOI, a plant to be infected is wounded, e.g. by cutting the plant with a razor or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known nethods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

In surnmation, a composition suitable for use as a foodstuff or in the preparation of a foodstuff is described. The composition comprises a PME; a first PME substrate; and a second PME substrate; wherein neither the first PME substrate nor the second PME substrate originates in situ from the other.

As indicated above, PME substrates, such as pectins obtained from natural plant sources, are generally in the form of a high ester pectin having a DE of about 70%. Sugar must be added to extracts containing these high ester PME substrates to provide sufficient soluble solids to induce gelling. Usually a minimum of 55% soluble solids is required. Syneresis tends to occur more frequently when the percentage soluble solids is less than 55%. When syneresis does occur, expensive additives must be used to induce gelling.

With the present invention we have found that it is surprisingly possible to induce gelation of an extract containing a high ester PME substrate by adding a second high ester PME substrate. The increased gelling capability of these combined high ester PME substrates at levels of soluble solids which are less than 50% is completely unexpected. The prior art has always taught that high ester pectins typically require a minimum soluble solid content of 55% before gelling can occur.

Thus, in accordance with the broadest aspect of this preferred embodiment of the present invention we provide an aqueous system in a solidified gel state having a soluble solids content of less than 50% w/w, wherein the gelling has occurred by use of a high ester PME substrate. In this aspect, the solidified gel state can be determined by the procedure mentioned in the Examples section (infra).

The present invention is distinguishable from the teachings of WO-A-94/25575 as that patent application does not disclose or even suggest a composition comprising a PME; a first PME substrate and a second PME substrate; let alone a composition wherein neither the first PME substrate nor the second PME substrate originates in situ from the other. The same is true regarding the teachings of JP-A-63/209533.

It is also to be noted that the teachings on page 12 (lines 6–14) of WO-A-94/25575 even point away from the present invention. In this regard, the term "vegetable or fruit based products" as used on lines 7 and 8 of WO-A-94/25575 does not explicitly disclose a PME substrate. Moreover, the subsequent sentence "Alternatively (with our emphasis), the natural content of pectin may be demethylated by use of the enzyme . . . " on lines 12 to 14 of WO-A-94/25575 clearly points out that the reaction medium envisaged by WO-A-94/25575 only involves one PME substrate, and not at least two PME substrates as is found in the present invention.

Protocols

Protocol I

Calcium Sensitivity Index (CF)

Calcium sensitivity is measured as the viscosity of a pectin dissolved in a solution with 57.6 mg calcium/g pectin divided by the viscosity of exactly the same amount of pectin in solution, but without added calcium. A calcium insensitive pectin has a CF value of 1.

4.2 g pectin sample is dissolved in 550 ml hot water with efficient stirring. The solution is cooled to about 20° C. and the pH adjusted to 1.5 with 1N HCl. The pectin solution is adjusted to 700 ml with water and stirred. 145 g of this solution is measured individually into 4 viscosity glasses. 10 ml water is added to two of the glasses (double determinations) and 10 ml of a 250 mM $CaCl_2$ solution is added to the other two glasses under stirring.

50 ml of an acetate buffer (0.5 M, pH about 4.6) is added to all four viscosity glasses under efficient magnetic stirring, thereby bringing the pH of the pectin solution up over pH 4.0. The magnets are removed and the glasses left overnight at 20° C. The viscosities are measured the next day with a Brookfield viscometer. The calcium sensitivity index is calculated as follows:

$$CF = \frac{\text{Viscosity of a solution with } 57.6 \text{ mg Ca}^{2+}/\text{g pectin}}{\text{Viscosity of a solution with } 0.0 \text{ mg Ca}^{2+}/\text{g pectin}}$$

Protocol II

Degree of Esterification (% DE)

To 50 ml of a 60% isopropanol and a 5% HCl solution is added 2.5 g pectin sample and stirred for 10 min. The pectin solution is filtered through a glass filter and washed with 15 ml 60% isopropanol/5% HCl solution 6 times followed by further washes with 60% isopropanol until the filtrate is free of chlorides. The filtrate is dried overnight at 80° C.

20.0 ml 0.5 N NaOH and 20.0 ml 0.5 N HCl is combined in a conical flask and 2 drops of phenolphtalein is added. This is titrated with 0.1 N NaOH until a permanent colour change is obtained. The 0.5 N HCl should be slightly stronger than the 0.5N NaOH. The added volume of 0.1 N NaOH is noted as $V_0$.

0.5 g of the dried pectin sample (the filtrate) is measured into a conical flask and the sample is moistened with 96% ethanol. 100 ml of recently boiled and cooled destined water is added and the resulting solution stirred until the pectin is completely dissolved. Then 5 drops of phenolphtalein are added and the solution titrated with 0.1 N NaOH (until a change in colour and pH is 8.5). The amount of 0.1 N NaOH used here is noted as $V_1$. 20.0 ml of 0.5 N NaOH is added and the flask shaken vigously, and then allowed to stand for 15 min. 20.0 ml of 0.5 N HCl is added and the flask is shaken until the pink colour disappears. 3 drops of phenolphtalein are then added and then the resultant solution is titrated with 0.1 N NaOH. The volume 0.1 N NaOH used is noted as $V_2$.

The degree of esterification (% DE: % of total carboxy groups) is calculated as follows:

$$\% DE = \frac{V_2 - V_0}{V_1 + (V_2 - V_0)}$$

Food Preparations
Introduction

By way of introduction, food compositions according to the present invention may comprise one or more other components, such as one or more food ingredients. Typical food ingredients include any one or more of an acid—such as citric acid—or a sugar—such as sucrose, glucose or invert sugar—or fruit, or enzymes.

For example, fruit imparts not only taste, colour and structure to the gel, but also pectin, acid and a small amount of solids. Depending on the level of natural flavour and colour in the fruit, fruit dosages are normally from 25% to 60% of the jam. The solids content of ordinary fruit is around 10% Brix, but fruit concentrate, which is typically 65–70% Brix, can also be used. The pH in fruit varies widely, depending on the fruit in question, but most fruits have a pH between 3.0 and 3.5.

The pectin content also varies, depending on the fruit in question. For example, redcurrants, blackcurrants and oranges have a high pectin content, and satisfactory gels from these fruits can be obtained by adding only a small amount of extra pectin. The choice of GRINDSTED™ Pectin depends on the type of jam in question. For example, GRINDSTED™ Pectin SS 200 is used in jams containing no fruit pieces or jam containing only very small fruit pieces. Fruit separation in such jams is not a problem, and consequently a slow-setting pectin and lower filling temperature can be used. GRINDSTED™ Pectin RS 400 is used in jams containina large fruit pieces or whole fruit, for instance cherries or strawberries. In jams containing whole fruit it may be difficult to avoid fruit separation, and it is therefore necessary to use a rapid-set pectin such as GRINDSTED™ Pectin RS 400.

The chioice of pectin type may also depend on the container size in question. When standard jars are used, the filling temperature is less critical with regard to the stability of pectin, as the jars will cool down relatively quickly after filling and the pectin will not degrade. However, if the jam is filled into large containers, eg 500 or 1,000 kg, the cooling time will be very long. In the centre of such a large container the pectin will be especially subject to degradation, and the gel will be weaker at the centre than at the sides. Consequently, a more slow-setting pectin is generally used for large containers, allowing filling at lower temperatures and thereby avoiding degradation of the pectin.

Sugar is added to jam for various reasons, such as:
1. To provide soluble solids—HE pectins can require a minimum soluble solids content of 55% before they will gel
2. To provide sweetness
3. To provide increased physical, chemical and microbiological stability
4. To provide an improved mouthfeel
5. To provide improved colour and gloss Sucrose is the sugar normally used, but other sugars may well be used depending on the taste, sweetening effect, crystallisation or structure required. Price may also influence which type of sugar is used.

Invert sugar has the same sweetening effect as sucrose, whereas glucose syrup, glucose and sorbitol have a reduced sweetening effect. High fructose corn syrup and fructose will have a greater sweetening effect than sucrose.

The structure and strength of the gel as well as the geiling temperature will, to some extent, be influenced by changes in sugar composition.

Acid is added for two reasons: 1) partly to reduce the pH level to 3.0–3.2 to obtain a satisfactory gel with the pectin, and 2) partly to enhance the flavour of the fruit. The optimum pH for gelation using the HE pectins depends on the type of pectin and solids content in question.

If GRINDSTED™ Pectin SS 200 is used in jam with 65–68% Brix, the optimum pH is 3.0–3.2.

If the solids content is higher than this, the optimum pH is 3.1–3.3.

Conversely, if the solids content is lower the optimum pH is 2.8–3.0.

If GRINDSTED™ Pectin RS 400 is used, the optimum pH is approximately 0.2 units higher than for GRINDSTED™ Pectin SS 200.

The acid most commonly used is citric acid, monohydrate, in a 50% w/v solution.

Other acids (such as malic acid, tartaric acid or phosphoric acid) may be used but must always be in solution.

The choice of acid depends on legislation, price, and the tartness of sweetness required in the finished product.

Citric acid imparts a relatively strong acid taste to the finished product, whereas malic acid results in a softer but longer-lasting taste.

Tartaric acid may result in a slightly bitter taste, and phosphoric acid results in a sweeter taste.

Enzymacically treated pectin can prevent syneresis which can often occur in the manufacture of marmalades and jams with low soluble solids contents.

Low Sugar Jam and Marmalade with 25% SS
Formulation

| Ingredients | % | % Soluble Solids |
|---|---|---|
| Pectin Pre-solution: | | |
| Enzyme modified pectin[1] (high Ca-reactive) | 0.6–0.8 | 0.6–0.8 |
| Sugar | 3.6 | 3.6 |
| Water | 18.0 | |
| Fruit Base: | | |
| PME[2] | 7–8 Units | |
| Fruit with natural pectin* | 45.0 | 4.5 |
| Sugar | 15.9 | 15.9 |
| Water | 21.1 | |
| Preservatives | As required | |
| Citric Acid** | As required | |
| Total | ~104 | |
| Evaporation | ~4 | |
| Yield | 100.0 | |
| Final soluble solids | 25 | ~25 |
| Final pH | 3.2 | |

*Typical fruit include strawberry, apple, cherry, citrus fruit and blackcurrant
**Or any other food acid
[1]The enzyme modified pectin can be that of WO-A-97/03574
[2]The PME can be that of WO-A-97/03574

Procedure
Pectin Solution Preparation
1. Dry mix enzyme modified pectin and sugar
2. Dissolve the pectin-sugar mix in hot water (80° C.), agitating well Jam
1. Fruit, sugar and water are mixed
2. The fruit mix is given a short boil and cooled to 40° C.
3. After cooling to 40° C., PME solution is added
4. Reaction time for the fruit mix is one hour
5. The fruit mix is heated to 85° C. for a few minutes, and the jam is evaporated to the desired SS content
6. The pectin solution is added
7. Preservatives are added and pH is adjusted
8. The jam is cooled to filling temperature, filled and cooled to room temperature This Example may be modified by the addition of or substitution with at least one other suitable food ingredient, and/or by the addition another suitable enzyme (such as a glucanase).

Low Sugar Jam and Marmalade with 50% SS
Formulation

| Ingredients | % | % Soluble Solids |
|---|---|---|
| Pectin Pre-solution: | | |
| Enzyme modified pectin[1] (high Ca-reactive) | 0.4–0.7 | 0.4–0.7 |
| Sugar | 2.2 | 2.2 |
| Water | 11.0 | |
| Fruit Base: | | |
| PME[2] | 7–8 Units | |
| Fruit with natural pectin* | 45.0 | 4.5 |
| Sugar | 42.7 | 42.7 |
| Water | 3.1 | |
| Preservatives | As required | |
| Citric Acid** | As required | |
| Total | ~105 | |
| Evaporation | ~5 | |
| Yield | 100.0 | |
| Final soluble solids | 50 | ~50 |
| Final pH | 3.2 | |

*Typical fruit include strawberry, apple, cherry, citrus fruit and blackcurrant
**Or any other food acid
[1]The enzyme modified pectin can be that of WO-A-97/03574
[2]The PME can be that of WO-A-97/03574

Procedure
Pectin Solution Preparation
1. Dry mix enzyme modified pectin and sugar
2. Dissolve the pectin-sugar mix in hot water (80° C.), agitating well Jam
1. Fruit and water are mixed
2. The fruit mix is given a short boil and cooled to 40° C.
3. After cooling to 40° C., PME solution is added
4. Reaction time for the fruit mix is one hour
5. The fruit mix is heated to 85° C. for a few minutes
6. The remaining sugar and the pectin solution is added, and the jam is evaporated to the desired SS content
7. The jam is cooled to filling temperature, filled and cooled to room temperature This Example may be modified by the addition of or substitution with at least one other suitable food ingredient, and/or by the addition another suitable enzyme (such as a glucanase).

Modifications to the present invention will be apparent to those skilled in the art. For example, and as indicated in the above examples, additional examples would include application of both PME and glucanase to obtain a pectin with a lower degree of esterification (eg a slow-set pectin).

Preparation of Plant PME Modified Orange Mash
Stage I

Orange pieces were homogenised in a blender and boiled for 15 minutes to inactivate any endogenous enzymes. After freeze/thawing, 20% (w/w) sugar was added and the orange mash was diluted 1:1 with preheated (95–100° C.) deionised water. The mash was transferred to glass beakers, its pH and temperature were adjusted to 7.0 (using 10% NaOH) and 40° C. respectively.

Purified plant PME (300 $\mu$mol/min/ml), at a concentration of (113 $\mu$l/200 g orange mash), was incubated with the mash at 40° C. for 15 minutes after which the pH was adjusted to 3.2 (+/−0.6) using citric acid (50% w/v). To inactivate the added plant PME, the mash was heat treated at 85° C. for 3 minutes. While plant PME activity typically requires the addition of NaCl for activity, this preparation of enzymatically modified orange mash did not require any exogenously added NaCl as sufficient endogenous NaCl (24 ppm) was present to ensure PME activity.

The plant PME treated mash (approximately 90 g) was stored in crystallisation dishes (diameter: 60 mm, height: 35 min) at 5° C. All pectin gelation measurements were performed within three days of processing and yielded reproducible results.

Stage II—Selection, Preparation and Addition of Pectin Substrates

Selection: Three pectin substrates were selected for use. All three substrates, GRINDSTED™ pectin SS200, P66 and P60 substrates had a high degree of esterification (% DE). These were 65%, 66% and 60% respectively. Both P60 and P66 were produced by plant PME pretreatment of GRINDSTED™ Ultra Rapid Set (URS) pectin whereas the GRINSTED™ pectin SS200 was untreated. Two of the three substrates. P60 and P66 were calcium sensitive whereas GRINSTED™ pectin SS200 has calcium insensitive. Only one of the substrates, GRINSTED™ pectin SS200, was commercially available.

Preparation: P66 and P60 were produced by plant PME pretreatment of GRINDSTED™ URS pectin using the following procedure: GRINDSTED™ URS pectin was solubilised in 0.15M NaCl and treated with plant PME for several hours at pH 7.0 at 40° C. After adjusting the pH to 3.0, the solubilised pectin was heated to 100° C. for 5–10 minutes, to inactivate any PME present, after which it was precipitated with isopropanol and dried before use. All three pectin substrates was prepared as an 8% solution and dissolved completely in preheated (80° C.) deionised water using a magnetic stirrer.

Addition: The addition of each pectin substrate to the plant PME enzymatically modified mash was performed using a high speed magnetic stirrer to ensure a homogeneous solution.

Stage III—Preparation and Addition of Calcium Citrate

Pectin gelation can be induced by adding calcium, either as a slurry or as a hydrate, at high temperatures. Ca-citrate ($C_{12}H_{10}Ca_3O_{14}4H_2O$) was added at a final concentration of 5 mM to the mixture.

Stage IV—Measurement of Gel Strength

The degree of pectin gelation/gel strength was determined by compression tests using a texture analyser. The methodology is described in "The Chemistry and Technology of Pectin" Ed. Reginald H Walker; Academic Press; (1991) p 240 (the contents of which are incorporated herein by reference).

Viscosity measurements, induced by compression, were performed on a SMS TA-XT2 Texture Analyser (Reciproter) using a cool stored (5° C.) probe (P 25/L), at a speed of 2.0 mm/sec and a penetration of 30%. The sample temperature was 5° C. The peak force in the compression curve shows the gel strength in newton units (N).

Stage V—Tests for Syneresis and Solidification

Syneresis is defined as the inability of a pectin gel to form a solid. A gel was considered to display syneresis if it did not remain intact after inversion of a reaction vessel containing the gel. A gel was considered to display solidification if it remained intact after inversion of a reaction vessel containing the gel. An intact gel displayed a very level surface compared with an non-intact gel.

Results

Characterisation of plant PME treated orange mash

Plant PME treatment of orange mash resulted in a high ester pectin with an average degree of esterification (% DE) of 55.2% (% DE was determined according to Protocol II).

TABLE I

Effect of Calcium (0.096/g Ca-citrate/100/g orange mash) and/or plant PME treatment on orange mash gel strength.

| Plant PME Treatment | Ca-Citrate (5 mM) | Gel Strength (N) | Solidified Gel Y/N |
|---|---|---|---|
| − | − | 0.175 | No |
| − | + | 0.234 | No |
| + | − | 0.227 | No |
| + | + | 0.226 | No |

The gel strength of extracted orange mash was slightly modified by either treatment with plant PME or the addition of calcium (Table I). However, the sequential treatment of orange mash with plant PME followed by the addition of calcium had no synergistic effect on the gel strength achieved. The visual inspection of the gels indicated that were all in liquid form.

These results demonstrate that, although plant PME treatment of orange mash resulted in a more homogeneous product in terms of its degree of esterification (% DE of 55.2%) and its responsiveness to low levels of endogenous calcium, the enzymatically modified mash did not respond to exogenously added calcium in terms of calcium gelation or increased gel strength.

These results also demonstrate that the reaction of plant PME treated orange mash, with either endogenous or exogenously added calcium ions, is not sufficient for a satisfactory increase in gel strength to take place.

The addition of a second pectin substrate, such as P66 or P60, to the plant PME modified mash, either in the presence or absence of calcium, induced substantial increases in gel strength compared with the untreated orange mash control (Table II; FIG. 1). Specifically, both P66 and P60 pectin substrates induced 3-fold and 5-fold increases in gel strength respectively, after addition of each substrate to the plant PME modified orange mash, in the presence of calcium. The fold increase in gel strength is slightly less pronounced for both pectin substrates in the absence of calcium in the reaction mix.

The addition of the GRINDSTED™ pectin SS200 substrate to the plant PME modified mash failed to induce a fold increase in gel strength as the GRINSTED™ pectin SS200 substrate was not PME pretreated and the combined substrates thus proved impossible to gel.

TABLE II

Effect of combined pectin substrates and calcium on gel strength achieved

| Pectin Type | % Pectin | % Soluble Solids | pH | Plant PME treated mash | Calcium Citrate (5 mM) | Gel Strength (N) | Relative Increase in Gel Strength | Solidified Gel Yes/No |
|---|---|---|---|---|---|---|---|---|
| Mash | | | | | 0 | 0.175 | 100 | No |
| SS200 | 0.8 | 20 | 3.1 | + | 0 | 0.195 | 111 | No |
| SS200 | 0.8 | 20 | 3.2 | + | + | 0.223 | 127 | No |
| P66 | 0.8 | 20 | 3.1 | + | 0 | 0.316 | 180 | Viscous |
| P66 | 0.8 | 20 | 3.1 | + | + | 0.457 | 312 | Yes |
| P60 | 0.8 | 20 | 3.1 | + | 0 | 0.530 | 302 | Yes |
| P60 | 0.8 | 20 | 3.1 | + | + | 0.782 | 446 | Yes |

A solidified gel was obtained after combining the P66 pectin substrate with plant PME modified orange mash in the presence but not in the absence of calcium. In contrast, solidified gels were induced after combining the P60 pectin substrate with plant PME modified mash either in the presence or absence of calcium.

Figure 2:
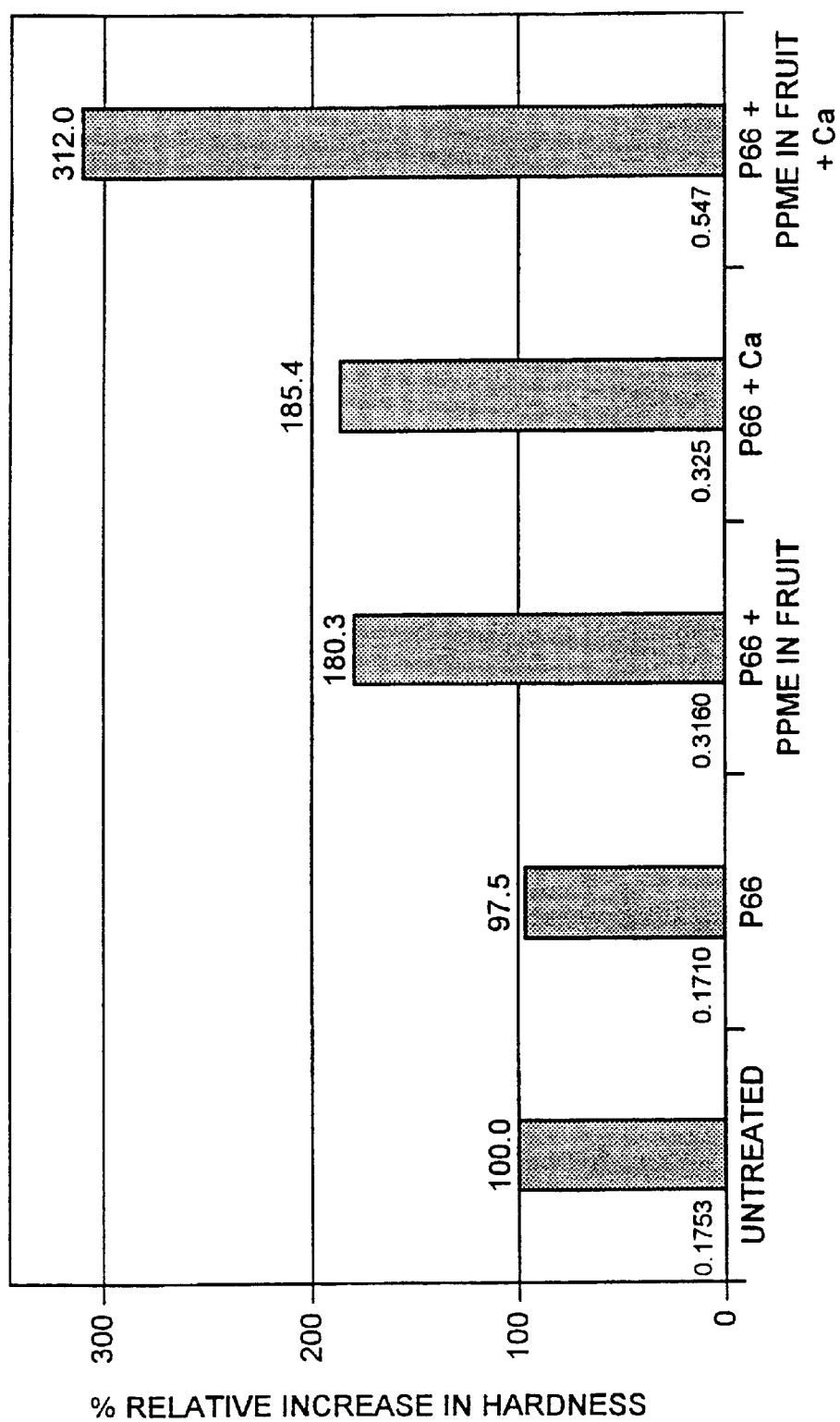
FIG. 2 is a bar chart showing the effect of PPME treatment of fruit and pectin (P66).

The additive effect of both PME treatment and the presence of calcium on pectin gelation is illustrated in FIG. 2. This figure sets out the percentage relative increase in gel strength (or hardness) observed When a P66 pectin substrate is added to either untreated or PME treated orange mash in the presence and absence of calcium. The actual values for gel strength (N) are shown next to each column and the percentage relative increase in gel strength is shown on the top of each column. Reading the figure from left to right, column one indicates that the untreated orange mash has a low gel strength which, on visual inspection, is in a liquid form. When a second pectin substrate, such as P66, is added to the untreated orange mash in the absence of calcium, there is no effect on the gel strength obtained (column 2). However, if P66 is added to plant PME treated orange mash an increase in gel viscosity is observed (column 3). A similiar increase in gel viscosity is observed by combining P66 with the untreated orange mash in the presence of calcium (column 4). Finally, if P66 is added to plant PME treated orange mash in the presence of calcium, a solidified gel is obtained (column 5). These results are obtained regardless of the sequence in which the combination and PME treatment of the substrates takes place. Thus, a solidified gel is obtained if a GRINSTED™ URS pectin substrate and an orange mash preparation are combined and PME treated in the presence of calcium or if a GRINSTED™ URS pectin substrate and an orange mash preparation are PME pretreated seperately before combination in the presence of calcium.

The experiments described in FIGS. 1 and 2 were repeated and the results are set out in Table III. A visual inspection of the gels produced from these experiments confirmed the earlier findings that:

(i) orange mash alone or after treatment with plant PME and calcium, either alone or in combination, will not induce an increase in gel strength.

(ii) The addition of calcium alone to GRINSTED™ URS pectin does not change the functionality of the pectin. Likewise, if GRINSTED™ URS pectin is not treated with plant PME, an increase in viscosity, but no solidification is observed when it is combined with plant PME treated orange mash either in the presence or absence of calcium.

(iii) The treatment of GRINSTED™ URS pectin with plant PME produces P66 which makes the pectin more functional when combined with plant PME treated orange mash in the presence of calcium. This increased functionality is indicated by the induction of solidification in the gel sample.

(iv) The treatment of two pectin substrates, such as orange mash and GRINSTED™ URS pectin with plant PME results in more functional high ester pectins, which in the presence of calcium, are capable of inducing solidification of a low solid jam.

TABLE III

Effect of combined pectin substrates and calcium on observed gel strength

| Pectin Type | Plant PME | % Pectin | % Soluble Solids | Plant PME treated/ untreated (+/−)mash | Calcium Citrate (5 mM) | Gel State |
|---|---|---|---|---|---|---|
| Mash | 0 | | | | 0 | Liquid |
| Mash | + | | | | + | Liquid/Viscous |
| Mash | 0 | | | | + | Liquid |
| Mash | + | | | | + | Liquid/Viscous |
| URS* | 0 | 0.8 | 20 | − | 0 | Liquid |
| URS* | 0 | 0.8 | 20 | − | + | Liquid/Viscous |
| URS* | 0 | 0.8 | 20 | + | 0 | Liquid/Viscous |
| URS* | 0 | 0.8 | 20 | + | + | Liquid/Viscous |
| P66 | — | 0.8 | 20 | − | 0 | Viscous |
| P66 | — | 0.8 | 20 | − | + | Viscous |
| P66 | — | 0.8 | 20 | + | 0 | Solidified |
| P66 | — | 0.8 | 20 | + | + | Solidified |

*is GRINSTED™ URS pectin

Discussion

When a low soluble solid jam is prepared from an orange mash homogenate, no gelling is observed even after plant PME treatment or the addition of exogenous calcium. Likewise, if a second high ester pectin substrate, such as P66, is added to an untreated orange mash preparation, it will have no effect on its gelling capability even if the second pectin substrate is made more functional by pretreating it with a plant PME enzyme. An increase in gel viscosity will be observed, however, if a second high ester pectin substrate, such as P66, is combined with untreated orange mash in the presence of calcium. A similiar effect, in terms of an increase in gel viscosity, is observed if the same high ester pectin substrate (P66) is combined with plant PME treated orange mash in the absence of calcium.

These results indicate that increases in gel viscosity can be induced by either plant PME treatment of orange mash prior to combination with a high ester pectin substrate such as P66 or by combining untreated orange mash with P66 in the presence of calcium. The results also indicate that the combination of plant PME treated orange mash with P66 in the presence of calcium will result in a solidified gel. This effect is obtained regardless of the sequence in which the combination and PME treatment of the substrates takes place. Thus, gel solidification will be observed by either PME pretreatment of the pectin substrates before combination or by PME treatment of the combined substrates in the presence of calcium.

SUMMARY

When a low soluble solid jam is prepared from orange mash, no gelling is observed even after the plant PME treatment of the orange mash or the addition of exogenous calcium.

If a second high ester pectin substrate is added to an untreated orange mash, t will have no effect on its gelling capability even if the second substrate is made more functional prior to addition by pretreatment with a plant PME enzyme.

The combination of plant PME treated orange mash with PME pretreated high ester pectin substrates, either in the presence or absence of calcium, will produce gels with substantially increased gel strength and improved functionality. Thus, PME treatment of pectin substrates, either alone or in combination, will improve their gelling capability by making the pectin substrates more functional as high ester substrates in the presence of calcium.

What is claimed is:

1. A gelling composition comprising a pectin methyl esterase (PME), a PME substrate and a high ester PME-treated pectin or a high ester PME-treated derivative of pectin, which high ester PME-treated pectin or high ester PME-treated derivative of pectin is sensitive to calcium ions, wherein neither the PME substrate nor the high ester PME-treated pectin or the high ester PME-treated derivative of pectin originates in situ from the other.

2. A composition according to claim 1 wherein the PME is recombinant.

3. A composition according to claim 1 wherein the PME substrate is pectin or a derivative thereof.

4. A composition according to claim 1 wherein the PME substrate is present within a plant or a plant material.

5. A composition according to claim 4 wherein the plant or plant material is selected from the group consisting of a vegetable, a vegetable material, a fruit, a fruit material, and combinations thereof.

6. A composition according to claims 5 wherein the vegetable material or the fruit material is a mash.

7. A composition according to claim 3 wherein the pectin or derivative thereof is a high ester pectin.

8. A composition according to claim 1 being in a solidified gel state and having a soluble solids content of less tan 50% w/w.

9. A method of preparing a composition comprising a pectin methyl esterase (PME) substrate and a calcium-sensitive high ester PME-treated pectin or a high ester PME-treated derivative of pectin, the method comprising treating 1) said PME substrate, and 2) said calcium-sensitive high ester PME-treated pectin or high ester PME-treated derivative of pectin with PME prior to, during and/or after combining said PME substrate and said calcium-sensitive high ester PME-treated pectin or high ester PME-treated derivative of pectin to form the composition, wherein neither said PME substrate nor said calcium-sensitive high ester PME-treated pectin or calcium-sensitive high ester PME-treated derivative of pectin originates in situ from the other.

10. A method according to claim 9 wherein the PME is recombinant.

11. A method according to claim 9 wherein the PME substrate is pectin or a derivative thereof.

12. A method of imparting stability to a composition comprising a pectin methyl esterase (PME) substrate, which process comprises adding to said composition at least 1) PME and 2) a calcium-sensitive high ester PME-treated pectin or a calcium-sensitive high ester PME-treated derivative of pectin wherein neither said PME substrate nor said calcium-sensitive high ester PME-treated pectin or calcium-sensitive high ester PME-treated derivative of pectin originates in situ from the other.

13. A composition obtained by the method of claim 9.

14. A composition according to claim 13 being in a solidified gel state and having a soluble solids content of less than 50% w/w.

15. A composition according to claim 5 wherein the vegetable material and the fruit material are a mash.

16. A method according to claim 9 wherein the PME substrate is present within a plant or a plant material.

17. A method according to claim 16 wherein the plant or plant material is any one or more of the group consisting of a vegetable, a vegetable material, a fruit or a fruit material.

18. A method according to claim 17 wherein the vegetable material or the fruit material is a mash.

19. A method according to claim 17 wherein the vegetable material and the fruit material is a mash.

* * * * *